United States Patent [19]

Timmermann

[11] Patent Number: 4,613,850
[45] Date of Patent: Sep. 23, 1986

[54] CIRCUIT ARRANGEMENT FOR CHECKING THE POSITION OF ELECTRODES

[75] Inventor: Hartwig Timmermann, Hamburg, Fed. Rep. of Germany

[73] Assignee: Medel Medizinische Elektronik Handelsges. mbH, Hamburg, Fed. Rep. of Germany

[21] Appl. No.: 632,711

[22] Filed: Jul. 20, 1984

[30] Foreign Application Priority Data

Dec. 23, 1983 [DE] Fed. Rep. of Germany ....... 3346744

[51] Int. Cl.$^4$ ............................................. G08B 21/00
[52] U.S. Cl. .................................... 340/686; 128/908; 340/653
[58] Field of Search ................... 128/908, 421, 303.13; 340/635, 653, 686

[56] References Cited

U.S. PATENT DOCUMENTS 4,088,141  5/1978  Niemi .............................. 128/908 X
4,177,819 12/1979  Kofsky et al. .................. 128/908 X
4,303,073 12/1981  Archibald ....................... 128/908 X
4,504,882  3/1985  Breton .............................. 128/908 X Primary Examiner—James L. Rowland
Assistant Examiner—Brian R. Tumm
Attorney, Agent, or Firm—Erwin S. Teltscher

[57] ABSTRACT

A circuit arrangement adapted for checking the position of electrodes on an object includes a treatment generator for periodically supplying treatment energy and a test impulse independent of the treatment energy to the electrodes. A transfer impedance of a certain magnitude exists between the electrodes; a voltage is developed across, and a current flows through the transfer impedance as a result of the test impulse. An evaluator evaluates the magnitude of the transfer impedance, and includes a test circuit connected to the electrodes for accepting the voltage and/or the current developed across, and flowing through the transfer impedance, respectively, and a warning signal emits a warning signal upon the magnitude of the transfer impedance exceeding or dropping below respective predetermined limit values.

13 Claims, 3 Drawing Figures

CIRCUIT ARRANGEMENT FOR CHECKING THE POSITION OF ELECTRODES

BACKGROUND OF THE INVENTION

The present invention relates to a circuit arrangement for checking the position of electrodes of an object, which is more particularly to be treated with electric energy supplied to the electrodes by a generator. In such an arrangement, the electrodes can slip out of a precise position and can e.g. come into contact with one another (short-circuit), drop (open), or have a too large or too small distance from one another or from the object. In certain circumstances, this can undesirably influence the supply of electric energy and in the simplest case this can lead to an inadequate action, but dangerous overloading is also possible. If e.g. the electrodes are used in a muscle stimulator, skin burns or scalds can occur.

SUMMARY OF THE INVENTION

The problem of the invention is to check the position of the electrodes, particularly in a continuous manner during the treatment process and in the case of an inadmissible variation in the electrode position a signal is emitted, so that intervention can take place either automatically or by the operating personnel.

According to the invention this problem is solved in that an electrical test pulse is periodically applied to the electrodes and the current or voltage caused by the test pulse on or in the transfer or transition impedence between the electrodes is checked by means of an evaluating device and on exceeding or dropping below respective predetermined limit values emits a warning signal.

If the transfer impedance only has resistive or an ohmic component, the current or voltage drop occurring during the test pulse can be evaluated, the transfer resistance determined and compared with a desired value, optionally set as a function of the particular treatment case.

Another solution of the invention is obtained in that the electrodes are at least approximately insulated relative to one another and consequently in the normal case the transfer impedance has an appreciable capacitive component, the load or voltage changes on the capacitive component resulting from the test pulse are determined in the evaluating means or device and on exceeding or dropping below respective predetermined limit values a warning signal is emitted.

On determining the ohmic and/or capacitive component of the transfer impedance by means of test pulses, the treatment energy can be fundamentally simultaneously supplied. If e.g. short wave energy with a frequency of approximately 27 MHz is supplied and the test pulses have a low frequency spectrum, e.g. a repetition frequency of 50 Hz, separation is possible through frequency separating means, such as frequency-dependent filters. The decoupling between the test pulses and the treatment energy is particularly simple if the generator has at least temporarily, e.g. by being inactivated or switched off, a high internal impedance and the test pulse is applied in these intervals of high generator internal impedance.

The decoupling is particularly simple if the test pulse is supplied when the treatment energy is not supplied, e.g. before switching on or in the periodic intervals between applications of treatment energy so that the supply of the test pulse energy is independent of the supply of the treatment energy.

A particularly preferred embodiment of the invention is characterized in that the test pulse is supplied to the electrodes as a current pulse and the voltage appearing at the electrodes during its duration is supplied to the evaluating device, which supplies a disconnection signal to the generator if the electrode voltage exceeds an upper limit value or drops below a lower limit value and/or if the capacitance of the capacitive component between the electrodes exceeds a predetermined maximum value and/or drops below a predetermined minimum value.

The warning signal is directly used for switching off the generator and upper and lower limit values can be fixed both for the ohmic and for the capacitive component of the transfer impedance.

Appropriately, the test pulse alternately has positive and negative polarity. This avoids a d.c. component flow through the treatment object, which could otherwise lead to electrolytic dissociation or other damage.

According to another embodiment, the capacitance can be determined by evaluating means evaluating the voltage change during the test pulse or immediately after its disconnection. As the test pulse leads to a charging or discharging of the capacitance, for the duration of the test pulse there is an approximately exponential voltage change at the transfer impedance. When the test pulse ceases, there is a load or charge change on the capacitance and a corresponding voltage change can be determined which, in accordance with the given time constant, also goes back again approximately exponentially. It is thus possible during the test pulse or after it has ceased to determine the course of the voltage curve by means of several test points and establish the capacitance therefrom. During the test pulse, the voltage then also contains the component resulting from the ohmic resistance whilst, after disconnecting the test pulse, it is only possible to determine the voltage at the capacitance. Thus, according to a simplified embodiment, the capacitance can be determined by evaluating the voltage immediately after the disconnection of the test pulse, it then being unnecessary to take account of the exponential potential gradient.

Finally, according to a further embodiment, the warning signal, e.g. its amplitude, can be dependent on the magnitude of the determined ohmic or capacitive component and can be supplied in regulating manner to a device for setting the electrode position, e.g. the distance from the object or the bearing pressure on the object, or a device for setting the electric energy supplied by the generator. Thus, within a given range of variations, it is possible to automatically make the necessary corrections without involving the operating personnel.

BRIEF DESCRIPTION OF THE DRAWINGS

The invention is described in greater detai hereinafter relative to a non-limitative embodiment and the attached drawings, wherein show.

DETAILED DESCRIPTION OF THE INVENTION

Figure 1:
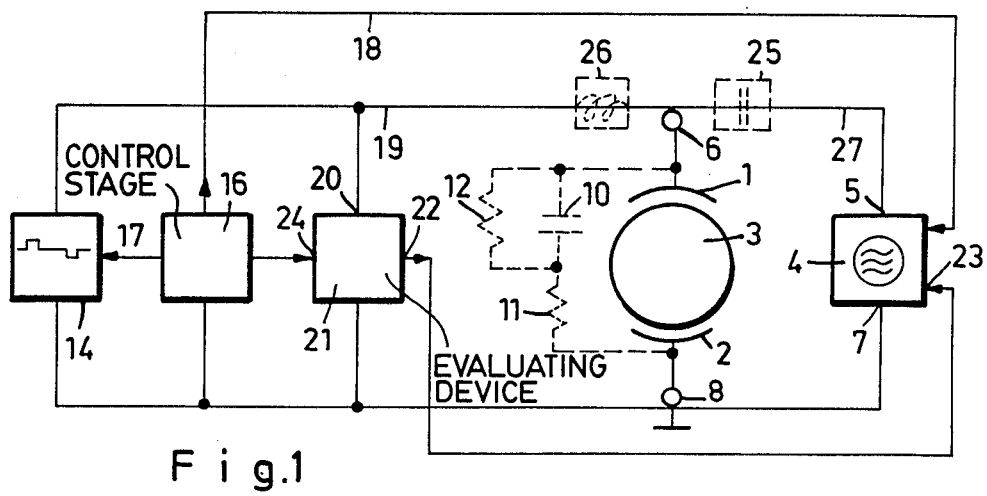
FIG. 1 a circuit arrangement according to the invention.

FIG. 1 shows a circuit arrangement according to the invention in a muscle stimulator. A first electrode 1 and a second electrode 2 are arranged on a treatment object 3, e.g. an upper arm muscle represented in cross-section through its contour line. Electric energy is supplied by a treatment generator 4 in its normally operative state to electrode 1 from its first output 5 via a first terminal 6 and to electrode 2 by its second output 7 via a second terminal 8. This energy can consist of pulses, whose width is adjustable between 10 and 990 μs and whose amplitude can be 160 $V_{ss}$ with alternating polarity. During the pulse, a constant current is supplied, which can be set between 1 and 99 mA. The frequency of these pulses can also be selected between 1 and 99 Hz. Thus, between the pulses is a gap in which the generator 4 is switched off i.e. by activatable statechanging means the state of the treatment generator is switched from its normally operative state to a non-operative state, so that it, supplies no energy and has a high internal resistance compared with the remaining switching part, so that in the intervals the generator branch does not have to be taken into consideration.

The distance between electrodes 1 and 2 can according to the equivalent circuit diagram shown in dotted line form, be represented as a series connection of a capacitor 10 of 0.47 μF and a resistor 11 of 1500 ohm, with a 220 ohm resistor 12 being parallel to capacitor 10. These are naturally specific values of a particular embodiment and in practice can vary considerably upwards and downwards in the individual case.

Test impulse supply means, such as a test signal generator 14 supplies test pulses to terminals 6 and 8 and consequently to electrodes 1 and 2 and corresponds to the 5 V power source with an internal resistance of 15 kOhm. Thus, with the given values, the test signal generator 14 supplies transfer impedance 10, 11, 12 with a virtually constant current, the test pulse being supplied for a duration of 220 μs in the intervals of the treatment pulses, in which generator 4 is switched off.

Such a test pulse is diagrammatically shown in the continuous line and with a current amplitude a. Particularly due to resistor 11, at the start of the pulse interval there is a voltage amplitude b1. As capacitor 10 is charged during the pulse, the voltage between points 6 and 8 increases and at the end of the pulse interval reaches the somewhat higher value c, so that the difference between c and b1 is due to the charging of the capacitor. If test pulse (a) ceases, the voltage represented by dotted lines in FIG. 2 instantaneously decreases by an amount b2 between terminals 6 and 8 where b2 equals about b1, because instantaneously the current ceases through resistor 11. The voltage (c-b2) from capacitor 10 is maintained and this then decays exponentially, roughly corresponding to the time constant due to capacitor 10 and resistor 12. The size of the capacitance can be determined from the exponential course of the dotted line curve during test pulses 15 or subsequent thereto, e.g. by amplitude measurements at several points. It may be adequate for the intended monitoring and warning signal means to evaluate only the residual voltage left after disconnecting the test pulse 15 for comparison with a desired value and optionally for forming the warning signal.

Figure 2:
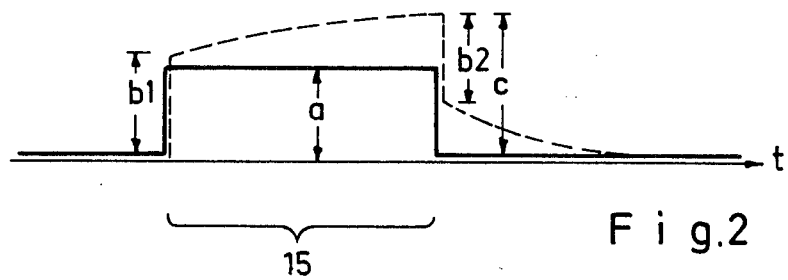
FIG. 2 the test pulse and in dotted line form the potential gradient occurring at the transfer impedance between the electrodes.

Control signals are supplied from a control stage 16 via a line 17 to a test pulse generator 14 and via a line 18 to the treatment generator 4 ensuring that the test pulses occur in the intervals of the treatment pulses. The voltage occurring during test pulses 15 at terminal 6 relative to the earth terminal 8 and which is shown in dotted line form in FIG. 2, is supplied by connecting line 19 between terminals 6 and test pulse generator 14 to an input 20 of evaluating means, such as an evaluating device 21. In the latter the amplitude values b1, c of the dotted line voltage curve in FIG. 2 are measured and prepared at least to preferably reach an adjustable desired value. This setting can take place as a function of the object to be treated, in order to ensure an optimum energy supply. If there is an inadmissible divergence from at least one desired value, a warning signal occurs at output 22 of evaluating device 21, which is supplied to the treatment generator 4 at input 23, switches off the generator and possibly releases a signal, e.g. a flashing lamp or bell. Control stage 16 can also supply the necessary sensing signals to an input 24, so that in evaluating device 21, the amplitude checking of the voltage between terminals 6 and 8 takes place at the correct time, which are to be selected for an appropriate evaluation.

Appropriately, means are provided so the test pulses have alternating polarity, so that they cannot cause a direct current through the treatment object.

Particularly if treatment energy is very high in the frequency range and low frequency test pulses are used, it can be admissible for the treatment energy to act continuously. Corresponding separating filters 25, 26 should then be connected in line 27 between terminal 6 and treatment generator 4 or in line 19 between terminal 6 and evaluating device 21 or test signal generator 14.

Figure 3:
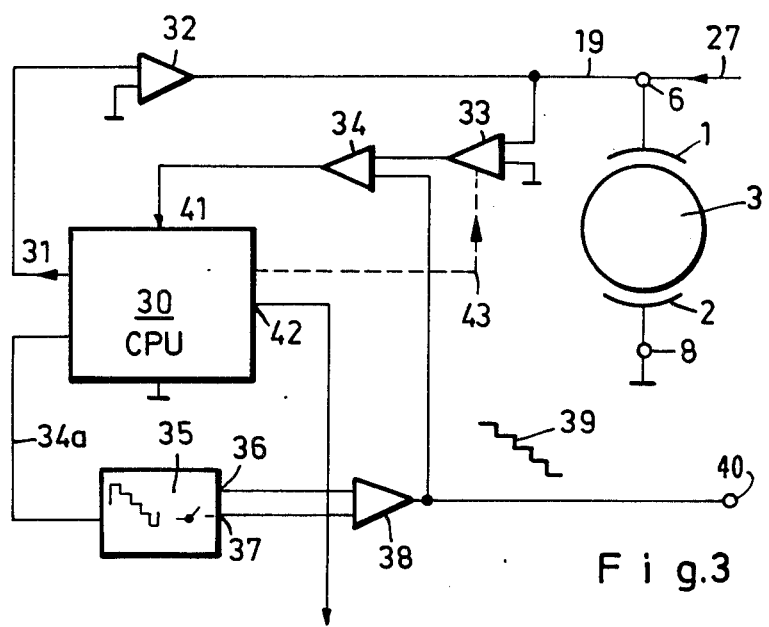
FIG. 3 a more detailed circuit diagram compared with FIG. 1 of an evaluating device and the stages associated therewith.

FIG. 3 again shows the object 3 between electrodes 1 and 2, which are connected to terminal 6 with lines 19, 27 and to terminal 8. The treatment generator 4 is omitted. The circuit according to FIG. 3 is controlled by evaluating means, such as a central unit 30, which in particular contains a sensing generator and supplies the necessary control and test signals, whilst also carrying out the evaluation of the voltage occurring at terminal 6 relative to terminal 8.

From output 31 of central unit 30, the test pulses are supplied to an amplifier 32 to whose output is connected line 19. The voltage occurring at terminal 6 is supplied to the input of a comparison amplifier 34 across amplifier 33. Via a line 34a, central unit 30 supplies control signals for a staircase generator 35, to whose outputs 36, 37 are connected the inputs of a differential amplifier 38. Amplifier 38 is controlled in such a way that a stair case voltage occurs at its output during test pulse 15 and is indicated by curve 39 in FIG. 3. This staircase voltage is supplied to a terminal 40 and can be used from there for other functions in the particular apparatus. Stair case voltage 39 is also supplied to the second input of comparison amplifier 34, which is e.g. set in such a way that it supplies an output pulse when the test voltage received from the output of amplifier 33 and supplied to the first input of amplifier 34 is higher than the staircase voltage 39 supplied to the second input. Thus, in accordance with the time position, at the output of comparison amplifier 34 a signal is received, which is representative of the particular amplitude stage. This signal is supplied to the input 41 of evaluation stage 30. Signal 39 preferably appears in the starting part of test pulse 15 and again immediately after the end thereof. Thus, two values are supplied to input 41, whereof the first substantially corresponds to the amplitude jump b in FIG. 2, whilst the second substantially corresponds to the amplitude jump (c-b2) in FIG. 2 immediately after the end of test pulse 15. The first amplitude jump gives information on the size of resistor 11 and central unit 30 supplies a warning signal at output 42 if this resistance value is above or below a set desired range.

The second amplitude jump represents the size of capacitor 10. This amplitude jump is also corresponding evaluated compared with predetermined desired values and if one of these limits is exceeded, a corresponding warning signal is supplied via output 42. As in FIG. 1, the warning signal can be used for switching off treatment generator 4 and for switching on a warning lamp or a warning bell.

As the amplitude (c-b2) of the exponential voltage range between terminals 6 and 8 caused by capacitor 10 can be much smaller than the voltage jump at the beginning or end of the test pulse caused by ohmic component 11, it can be appropriate to switch the gain of amplifier 33 to a higher, e.g. triple value for determining the exponential drop after the end of the test pulse. This can be brought about by central unit 30 via connection 43 to amplifier 33.

What is claimed is:

1. A circuit arrangement adapted for checking the position of electrodes on an object, comprising in combination a treatment generator for periodically supplying treatment energy and periodically supplying a test impulse independent of said treatment energy to the electrodes, and wherein a transfer impedance of a certain magnitude exists between said electrodes, a voltage being developed across, and a current flowing through said transfer impedance as a result of said test impulse, evaluating means for evaluating the magnitude of said transfer impedance, including test circuit means connected to said electrodes for accepting at least one of said voltage and current developed across, and flowing through said transfer impedance, respectively, and warning signal means for emitting a warning signal upon the magnitude of said transfer impedance exceeding or dropping below respective predetermined upper and lower limit values.

2. A circuit arrangement according to claim 1, wherein said treatment generator has an operative state and a nonoperative state, and further including test impulse supply means for supplying said test impulse to said electrodes, when said treatment generator is in said non-operative state.

3. A circuit arrangement according to claim 2, wherein said treatment generator has a high internal impedance during said non-operative state, and wherein said test impulse supply means supply said test impulse to said electrodes during the non-operative state of said treatment generator.

4. A circuit arrangement according to claim 2, wherein at least one of said treatment generator and said test impulse supply means includes means for alternately changing the polarity of said test impulse from a positive value to a negative value.

5. A circuit arrangement according to claim 2, wherein at least one of said treatment generator and said supply means includes means for inactivating said test impulse, and wherein said evaluating means further includes means for evaluating the magnitude of said transfer impedance by evaluating any change in the voltage developed across said transfer impedance immediately following inactivation of said test impulse.

6. A circuit arrangement according to claim 2, wherein at least one of said treatment generator and said supply means includes means for inactivating said test impulse, wherein said transfer impedance has a capacitative component of a certain magnitude, and wherein said evaluating means further includes means for evaluating the magnitude of said capacitative component by evaluating any change in the voltage developed across said transfer impedance immediately following inactivation of said test impulse.

7. A circuit arrangement according to claim 2, wherein said treatment generator supplies treatment energy at a relatively high frequency, and wherein said test pulse has a frequency spectrum which is low compared to the high frequency of said treatment energy, and further comprising first electrically conductive line means connecting said treatment generator to one of said electrodes, and second electrically conductive line means connecting said one of said electrodes to at least one of said test impulse supply means, and said evaluating means, each of said line means comprising respective frequency separating filter means so as to supply the low frequency test impulse to said evaluating means, while supplying said relatively high frequency from said treatment generator to the object to be treated.

8. A circuit arrangement according to claim 1, wherein said transfer impedance has a capacitative component of a certain magnitude, and wherein said treatment generator has a normally operative state and a non-operative state, and wherein said evaluating means further includes means for evaluating the magnitude of said capacitative component, and activatable state-changing means for changing the state of said treatment generator from the normally operative state to said non-operative state, said state-changing means including means for delivering a disconnect signal to said treatment generator so as to change its state from the normally operative state to said non-operative state upon the magnitude of said capacitative component exceeding said upper limit value, or dropping below said lower limit value.

9. A circuit arrangement according to claim 8, wherein said means for evaluating the capacitative component of said transfer impedance include means for evaluating any change in the voltage developed accross said transfer impedance.

10. A circuit arrangement according to claim 1, further comprising adjustment means for adjusting the position of said electrodes, and wherein said transfer impedance has a resistive component and a capacitative component of a certain magnitude, and wherein the signal emitted by said warning signal means is dependent on the magnitude of at least one of said resistive and capacitative components, and the adjusted position of said electrodes.

11. A circuit arrangement according to claim 10, wherein said electrodes are spaced at a certain distance from one another, and wherein said adjustment means comprises means for changing the distane between said electrodes.

12. A circuit arrangement according to claim 10, wherein said electrodes apply a certain pressure to said object, and wherein said adjustment means comprises means for changing said pressure applied to said object.

13. A circuit arrangement according to claim 1, wherein said treatment generator has a normally operative state and a non-operative state, and wherein said evaluating means accepts the voltage developed across said transfer electrodes, said evaluating means further including activatable state-changing means for changing the state of said treatment generator from the normally operative state to said non-operative state, said state-changing means including means for delivering a disconnect signal to said treatment generator so as to change its state from the normally operative state to said non-operative state upon the voltage developed across said transfer impedance exceeding said upper limit value, or dropping below said lower limit value.

* * * * *